(12) United States Patent
Hong

(10) Patent No.: US 11,147,543 B2
(45) Date of Patent: Oct. 19, 2021

(54) RETRACTOR FOR ENDOSCOPIC SURGERY

(71) Applicant: AFSMEDICAL GmbH Medizinproduktehandel, Teesdorf (AT)

(72) Inventor: Du Pyo Hong, Gimpo-si (KR)

(73) Assignee: AFSMEDICAL GMBH MEDIZINPRODUKTEHANDEL, Teesdorf (AT)

( * ) Notice: Subject to any disclaimer, the term of this patent is extended or adjusted under 35 U.S.C. 154(b) by 117 days.

(21) Appl. No.: 16/393,253

(22) Filed: Apr. 24, 2019

(65) Prior Publication Data

US 2019/0336119 A1 Nov. 7, 2019

(30) Foreign Application Priority Data

May 4, 2018 (KR) .................. 10-2018-0051564

(51) Int. Cl.
*A61B 1/32* (2006.01)
*A61B 1/015* (2006.01)
(Continued)

(52) U.S. Cl.
CPC ...... *A61B 17/0218* (2013.01); *A61B 17/0293* (2013.01); *A61B 17/3423* (2013.01); *A61B 17/3439* (2013.01); *A61B 2017/3445* (2013.01)

(58) Field of Classification Search
CPC .......... A61B 17/3423; A61B 17/3429; A61B 17/3439; A61B 17/3445; A61B 17/0293; A61B 2017/3411; A61B 2017/3466; A61B 17/3474; A61B 1/015; A61B 2218/001; A61B 2218/002; A61B 2218/005; A61B 2218/006; A61B 2218/007;
(Continued)

(56) References Cited

U.S. PATENT DOCUMENTS

2006/0247500 A1* 11/2006 Voegele ............. A61B 17/3417
600/208
2010/0185139 A1* 7/2010 Stearns ............. A61B 17/3474
604/26
(Continued)

FOREIGN PATENT DOCUMENTS

KR 20100057560 5/2010
KR 101037644 B1 * 5/2011 ......... A61B 17/3474
(Continued)

*Primary Examiner* — Jan Christopher L Merene
(74) *Attorney, Agent, or Firm* — Cantor Colburn LLP

(57) ABSTRACT

Provided is a retractor for endoscopic surgery, and more particularly, to a retractor for endoscopic surgery, the retractor being configured to supply and discharge gas to and from a human body, or directly to and from a human body. The retractor includes: a penetrating member penetrating through a human body; an anti-separation member provided at a lower portion of the penetrating member to prevent separation of the retractor from the human body; and a supply and exhaust member for supplying or exhausting gas, wherein the anti-separation member is provided with at least one of a supply hole to supply gas to the human body and an exhaust hole to exhaust gas from the human body by communicating with the supply and exhaust member, whereby gas supply or gas exhaust is preformed through the anti-separation member.

1 Claim, 5 Drawing Sheets

(51) Int. Cl.
*A61B 17/02* (2006.01)
*A61B 17/34* (2006.01)

(58) Field of Classification Search
CPC ............ A61B 2218/008; A61M 13/00; A61M 13/003; A61M 13/006
See application file for complete search history.

(56) References Cited

U.S. PATENT DOCUMENTS

| | | |
|---|---|---|
| 2010/0249694 A1 | 9/2010 | Choi et al. |
| 2010/0312066 A1* | 12/2010 | Cropper ............ A61B 17/3423 600/207 |
| 2013/0060094 A1 | 3/2013 | Lee |
| 2017/0007295 A1 | 1/2017 | Geisz |
| 2018/0256830 A1* | 9/2018 | Silver ................. A61M 13/006 |
| 2019/0110786 A1* | 4/2019 | Ip ....................... A61B 17/0218 |

FOREIGN PATENT DOCUMENTS

| | | |
|---|---|---|
| KR | 101525126 | 6/2015 |
| KR | 101815689 | 1/2018 |
| KR | 20180023525 | 3/2018 |
| WO | 2010141673 | 12/2010 |
| WO | 2016105214 | 6/2016 |

\* cited by examiner

RETRACTOR FOR ENDOSCOPIC SURGERY

BACKGROUND OF THE INVENTION

Field of the Invention

The present invention relates generally to a retractor for endoscopic surgery, in which the retractor defines a space by expanding a through-hole punctured in a human body during endoscopic surgery so as to allow a surgical instrument to be inserted through the through-hole. More particularly, the present invention relates to a retractor for endoscopic surgery, the retractor being configured to supply and discharge gas to and from the human body, or directly to and from the human body.

Description of the Related Art

In general, when performing endoscopic surgery, a through-hole is punctured in a human body instead of cutting a patient's body, and a retractor is coupled to the punctured through-hole to expand a diameter of the through-hole, so that surgical instruments (endoscopes, scissors, forceps, cameras, etc.) can be inserted through the retractor.

Further, gas is injected into the human body through the retractor to secure a surgical space in the human body, and when the human body is full of smoke and a field of view of a camera for surgery is interfered with, fresh gas is injected into the human body while the smoke inside the body is discharged to the outside, thereby removing the smoke from the human body.

There have been disclosed various types of retractor for endoscopic surgery in Korean Patent Application Publication No. 10-2018-0023525, Korean Patent No. 10-1525126, Korean Patent No. 10-1815689, and the like.

Although there are various types of retractor for endoscopic surgery, a retractor fundamentally includes: a penetrating member penetrating through a through-hole punctured in the human body; an anti-separation member at a lower portion of the penetrating member to prevent undesirable separation of the retractor from the through-hole of the human body; and a guide member provided at an upper portion of the penetrating member to guide an insertion of a surgical instrument.

The conventional retractor for endoscopic surgery is configured such that the guide member is provided with a supply nozzle for supplying gas, and an exhaust nozzle for exhausting gas, so the gas supplied by the supply and exhaust member is supplied into the guide member through the supply nozzle and then is supplied to the human body through the penetrating member; and the gas in the human body is discharged to the guide member through the penetrating member and then is discharged to the outside through the exhaust nozzle.

The conventional art is problematic in that since the gas is supplied to the human body and is discharged to the outside through the supply nozzle and the exhaust nozzle provided in the guide member, the smoke in the human body (gas including smoke) may be not removed efficiently.

In the case where smoke is generated in the human body during the endoscopic surgery and the field of view of a camera is not ensured, clean air (gas) from the outside is injected into the human body while gas in the human body (that is, smoke) is discharged to the outside, thereby maintaining the pressure inside the human body.

Here, in the case where the air in the guide member is discharged to the outside while air (gas) is injected in the guide member through the supply nozzle and the exhaust nozzle, the air injected in the guide member through the supply nozzle fails to be supplied into the human body via the penetrating member, but is more likely to be introduced from inside the guide member directly to the exhaust nozzle and discharged to the outside (see FIG. 5).

In other words, there must be an exchange of air in which clean air is injected in the human body and smoke in the human body is discharged to the outside, but instead, the clean air supplied to the penetrating member through the supply nozzle is discharged to the outside through the exhaust nozzle while hindering the smoke in the human body from being discharged.

The conventional art is further problematic in that a tube connected to the supply nozzle and the exhaust nozzle of the penetrating member respectively interferes with surgery.

In other words, since a practitioner performs surgery while changing a position, and accordingly, the direction of the surgical instrument is changed from time to time, and the retractor is rotated from time to time and the direction thereof is changed, the tube encumbers and interferes with the movement of the practitioner and surgical instrument.

Further, another conventional art is disclosed in Korean Patent Application Publication No. 10-2010-0057560.

In Korean Patent Application Publication No. 10-2010-0057560, there has been disclosed a retractor being configured such that a supply nozzle and an exhaust nozzle for supplying and exhausting air are coupled to an outside of an anti-separation member for preventing separation of the retractor from the human body, whereby the supply and exhaust is smoothly performed, and a tube connected to the supply nozzle and the exhaust nozzle interferes less with surgery.

However, according to Korean Patent Application Publication No. 10-2010-0057560, it is troublesome to connect and separate the supply nozzle and the exhaust nozzle to and from the anti-separation member by using a coupling mechanism such as a band or a clamp, and when the anti-separation member protrudingly provided with the supply nozzle and the exhaust nozzle is inserted into a human body or removed from the human body, the supply nozzle and the exhaust nozzle may interfere with insertion and removing, and skin damage may occur in the process.

The foregoing is intended merely to aid in the understanding of the background of the present invention, and is not intended to mean that the present invention falls within the purview of the related art that is already known to those skilled in the art.

Documents of Related Art (Patent document 1) Korean Patent Application Publication No. 10-2018-0023525,
(Patent document 2) Korean Patent No. 10-1525126,
(Patent document 3) Korean Patent No. 10-1815689, and
(Patent document 4) Korean Patent Application Publication No. 10-2010-0057560.

SUMMARY OF THE INVENTION

Accordingly, the present invention has been made keeping in mind the above problems occurring in the conventional retractor for endoscopic surgery, and an object of the present invention is to provide a retractor for endoscopic surgery, in which supply and discharge of gas to and from a human body is performed quickly, surely, and stably, a risk that the supplied gas and the discharged gas collide with each other to cause a problem is fundamentally prevented, and a tube supplying and discharging gas does not interfere with surgery.

In order to achieve the above object, according to some aspect of the present invention, there is provided a retractor for endoscopic surgery, the retractor including: a penetrating member penetrating through a human body; an anti-separation member provided at a lower portion of the penetrating member to prevent separation of the retractor from the human body; and a supply and exhaust member for supplying or exhausting gas, wherein the anti-separation member is formed with least one of a supply hole to supply gas to the human body and an exhaust hole to exhaust gas from the human body by communicating with the supply and exhaust member, whereby gas supply or gas exhaust is preformed through the anti-separation member.

The anti-separation member may be formed with both the supply hole and the exhaust hole, and the supply hole and the exhaust hole may be separated from each other.

The anti-separation member may be provided with a supply nozzle and an exhaust nozzle to respectively connect the supply hole and the exhaust hole to a tube of the supply and exhaust member.

According to the retractor for endoscopic surgery of the present invention, since the anti-separation member inserted into the human body is formed with at least one of the supply hole and the exhaust hole connected with the supply and exhaust member, or formed with both the supply hole and the exhaust hole, supply and discharge of gas is performed quickly, surely, and stably by directly supplying and discharging gas to and from the human body, and it is possible to fundamentally prevent a risk that the supplied gas and the discharged gas collide with each other to cause a problem. In addition, since the tube supplying and discharging gas is directly inserted into the through-hole of the human body and is arranged in a low level by being brought into contact with the surface of the human body, it is possible to minimize interference with the surgery by the tube, so the present invention is very useful for industrial development.

BRIEF DESCRIPTION OF THE DRAWINGS

The above and other objects, features, and other advantages of the present invention will be more clearly understood from the following detailed description when taken in conjunction with the accompanying drawings, in which.

DETAILED DESCRIPTION OF THE INVENTION

Figure 1:
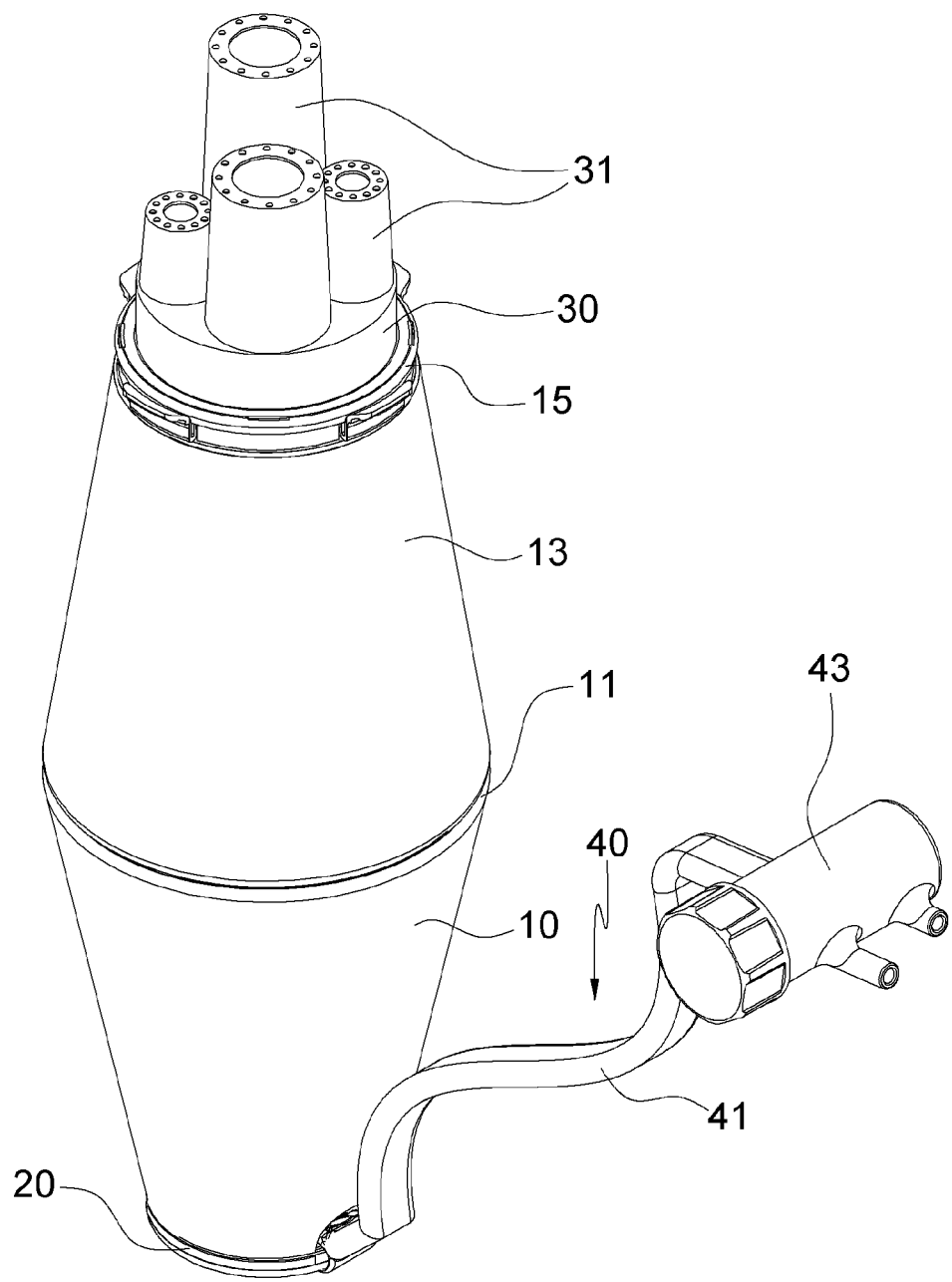
FIG. 1 is a perspective view showing an example of a retractor for endoscopic surgery according to the present invention.
Figure 2:
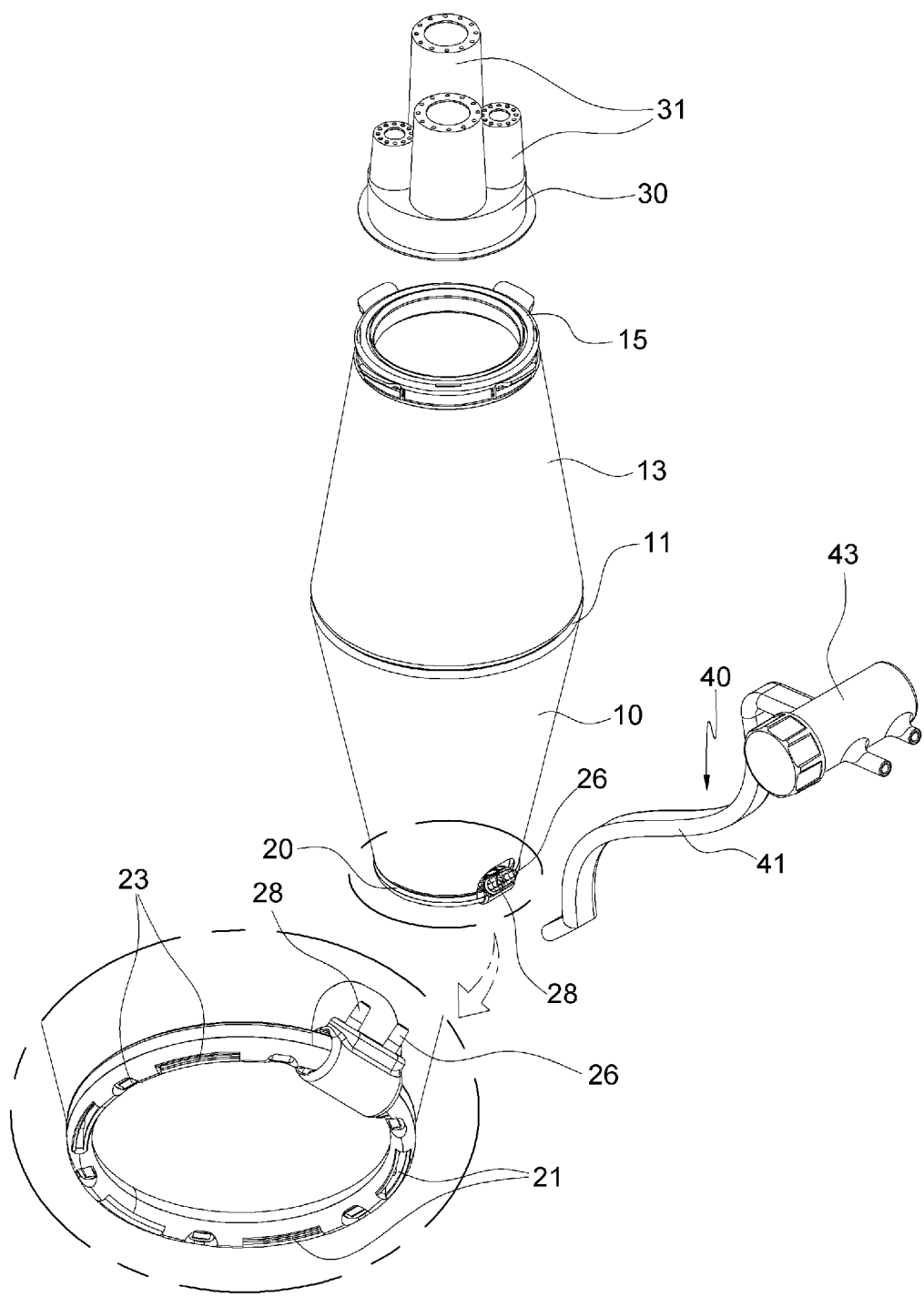
FIG. 2 is an exploded perspective view of FIG. 1.

Hereinbelow, reference will be made in detail to a retractor for endoscopic surgery according to the present invention, with reference to the accompanying drawings.

Before describing the retractor for endoscopic surgery of the present invention in more detail, the present invention will be described in detail based on aspects (or embodiments). The present invention may, however, be embodied in many different forms and should not be construed as being limited to only the embodiments set forth herein, but should be construed as covering modifications, equivalents or alternatives falling within ideas and technical scopes of the present invention.

In the figures, like reference numerals, particularly, tens and units, or reference numerals having like tens, units and letters refer to like elements having like functions throughout, and unless the context clearly indicates otherwise, elements referred to by reference numerals of the drawings should be understood on the basis of this standard.

Also, for convenience of understanding the elements, in the figures, sizes or thicknesses may be exaggerated to be large (or thick), may be expressed to be small (or thin), or may be simplified for clarity of illustration, but due to this, the protective scope of the present invention should not be interpreted narrowly.

The terminology used herein is for the purpose of describing particular aspects (or embodiments) only and is not intended to be limiting of the present invention. As used herein, the singular forms are intended to include the plural forms as well, unless the context clearly indicates otherwise. It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

Referring to the drawings, a retractor for endoscopic surgery according to the present invention includes: a penetrating member 10, an anti-separation member 20, a guide member 30, and a supply and exhaust member 40.

The penetrating member 10 penetrates through a through-hole punctured in a human body 1 for endoscopic surgery, and expands the diameter of the through-hole to form a passage that allows a surgical instrument to be inserted into the human body 1 through the through-hole (specifically, through the inside of the penetrating member 110 penetrating through the through-hole).

The penetrating member 10 is usually made of hard material in the case of a trocar, and is usually made of a soft material in the case of a retractor.

In the drawings, it is shown that the penetrating member is made of a soft material such as silicone and has a cylindrical structure.

The anti-separation member 20 is provided at a lower portion of the penetrating member 10 and is inserted into the human body through the through-hole punctured in the human body.

The anti-separation member 20 has a diameter of about 5 mm to 10 mm and is formed in an annular ring shape so as to be caught on an inner wall of the human body to ensure the retractor is not easily detached from the human body when impact is applied to the retractor in unintended situations.

The guide member 30 is provided at an upper portion of the penetrating member 10 to guide the surgical instrument to be inserted into the human body through the penetrating member 10.

The guide member 30 is provided with a port 31 for tightly covering the outer surface of the surgical instrument to prevent leakage of gas. Here, a plurality of ports 31 may be provided to be used for various types of surgical instruments.

Referring to the drawing, the upper portion of the penetrating member 10 is provided with an outer ring 11 that is caught outside the periphery of the through-hole of the human body; the upper portion of the outer ring 11 is connected with a soft movable member 13 to widen the movable radius so that the inserted surgical instrument can be moved more freely; and the upper portion of the movable member 13 is provided with a coupler 15 to which the guide member 30 is detachably coupled.

The supply and exhaust member 40, which is a mechanism that supplies gas to the human body or discharges gas in the human body to the outside, includes: a tube 41 for providing a passage through which gas is supplied and discharged; a filter 43 connected to the tube 41 to filter and remove foreign matter of the gas supplied to the human body; and a supply and exhaust pump (not shown) connected to the filter 43 and configured to provide power to supply or discharge the gas.

In order to directly supply and discharge gas to and from the human body, the present invention is configured such that the anti-separation member 20 inserted inside the human body is formed with a supply hole 21 for supplying gas, an exhaust hole 23 for exhausting gas, and a supply nozzle 26 and an exhaust nozzle 28 communicating with the supply hole 21 and the exhaust hole 23, respectively, and also with the tube 41.

As described above, the present invention supplies gas directly to the human body through the supply hole 21 formed in the anti-separation member 20 inserted into the human body, and discharges gas directly from the human body through the exhaust hole 23, so that the supply and discharge of the gas can be performed quickly, surely, and stably, and when smoke is removed, it is possible to prevent an accident that the smoke is not exhausted due to the collision between the supplied gas and the exhausted gas.

Further, according to the present invention, the tube 41, which provides the passage through which gas is supplied and discharged, is brought into contact with the surface of the human body and is arranged in a low level, thereby minimizing the interference with the practitioner's movement and the movement of the surgical instrument at the time of surgery, thus facilitating the surgery.

Figure 3:
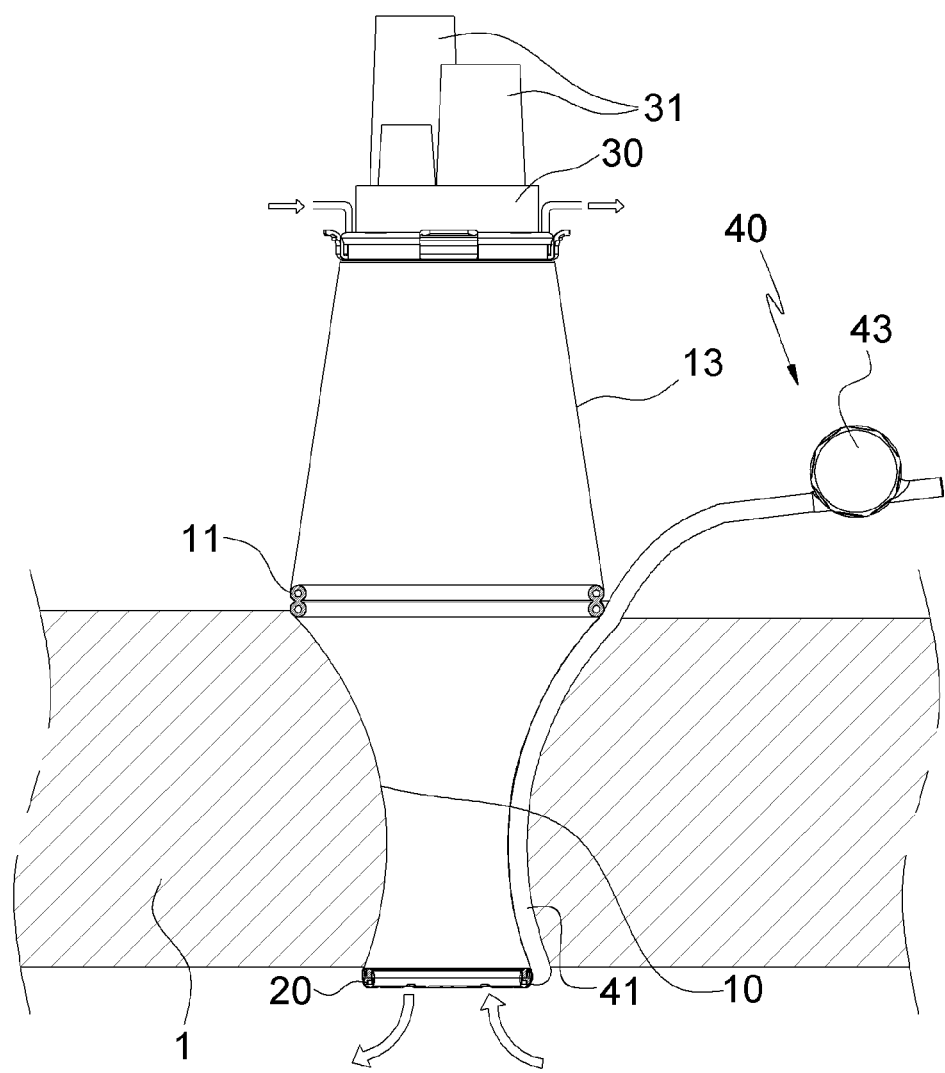
FIG. 3 is a view showing an example where the retractor of FIG. 1 is coupled to a through-hole of a human body.
Figure 4:
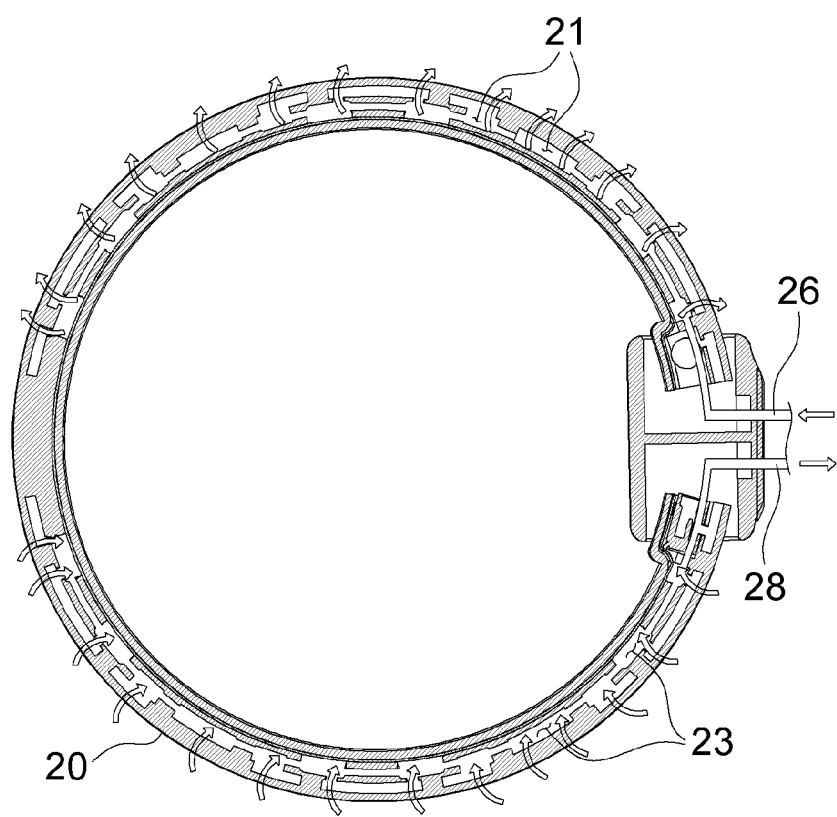
FIG. 4 is a sectional view showing an anti-separation member formed with a supply hole and an exhaust hole.

Referring to FIGS. 3 and 4, the internal space of the human body 1 in which the anti-separation member 20 is inserted is spacious. Thus, even though gas is simultaneously supplied and discharged through the supply hole 21 and the exhaust hole 23 of the anti-separation member 20, the supply and discharge of the gas is not interfered with by the collision between the supplied gas and the exhausted gas.

Figure 5:
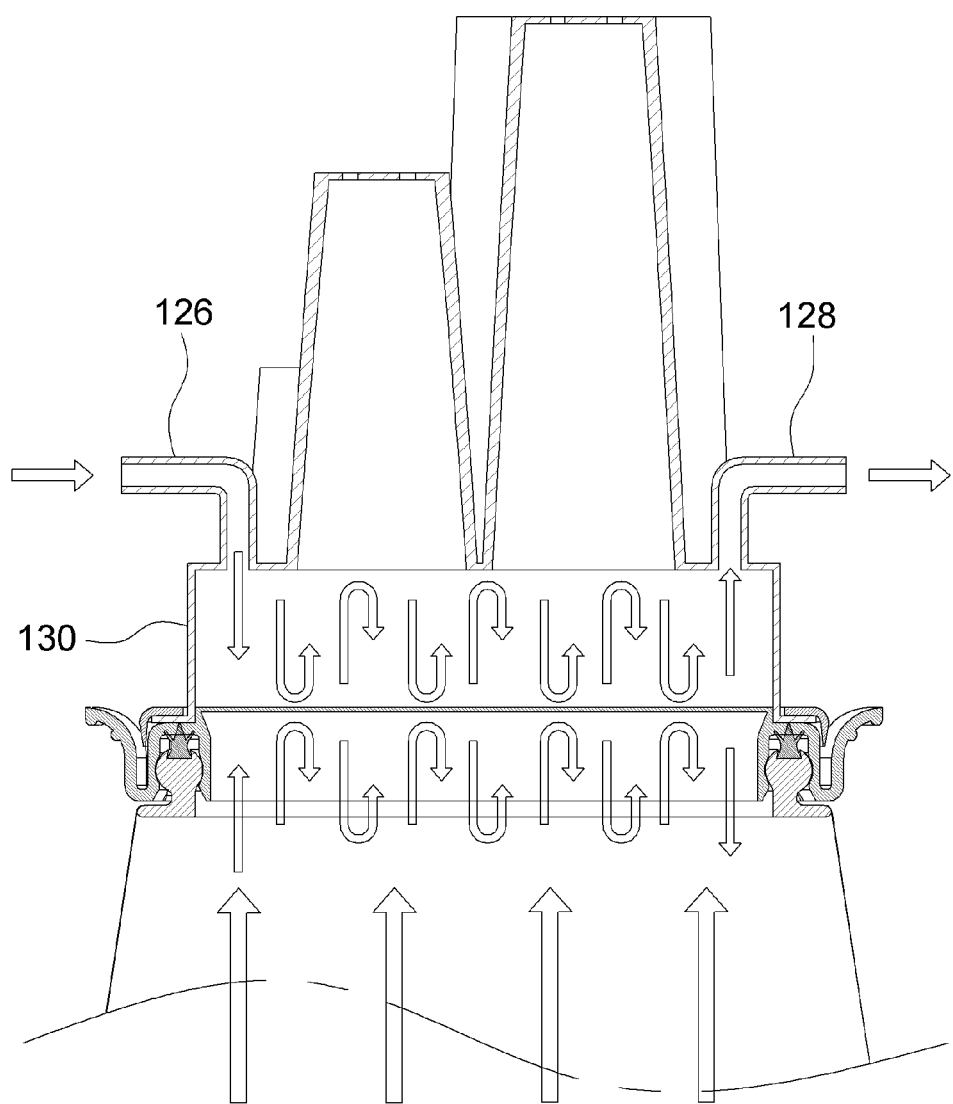
FIG. 5 is a view showing a state where the air supplied from a supply nozzle is discharged to an exhaust nozzle without being injected into a human body in a conventional art.

On the contrary, referring to FIG. 5, as in the conventional art, when a supply nozzle 126 and an exhaust nozzle 128 are provided in a guide member 130, gas is supplied from the supply nozzle 126 to the guide member 130, and gas in the human body is sucked into the guide member 130 in order to discharge the gas to the exhaust nozzle 128. Herein, since the internal space of the guide member 130 is narrow, the supply gas supplied from the supply nozzle 126 and the exhaust gas discharged from the human body collide with each other, and thus, the colliding exhaust gas is blocked by the supply gas and is no longer discharged, and the colliding supply gas is diverted and discharged to the exhaust nozzle 128. Here, the continuously supplied supply gas continuously interferes with the discharge of the exhaust gas.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A retractor for endoscopic surgery, the retractor comprising:
   a cylindrical penetrating member being capable of penetrating through a through-hole of a human body, wherein the penetrating member is configured to expand the through-hole to form a passage allowing a surgical instrument to be inserted into the human body through the through-hole;
   an annular anti-separation member attached to a lower end portion of the cylindrical penetrating member, wherein the annular anti-separation member is configured to prevent separation of the cylindrical penetrating member from the human body when the cylindrical penetrating member is penetrated into the through-hole;
   a supply and exhaust member including: a first tube and a second tube coupled to the annular anti-separation member, wherein the supply and exhaust member is configured to supply a first gas to the annular anti-separation member through the first tube and discharge a second gas from the annular anti-separation member through the second tube,
   wherein the annular anti-separation member includes:
      a supply conduit;
      a plurality of supply holes formed in the annular anti-separation member and along the supply conduit, through which the first gas is able to be supplied into the human body from the annular anti-separation member;
      an exhaust conduit;
      a plurality of exhaust holes formed in the annular anti-separation member and along the exhaust conduit, through which the second gas is able to be exhausted from the human body into the annular anti-separation member;
   a supply nozzle through which the first gas is supplied into the annual anti-separation member from the first tube, a first end of the supply nozzle formed within the annular anti-separation member and fluidly coupled to the supply conduit, a second end of the supply nozzle extending form the annular anti-separation member and adapted to couple to the first tube;
   an exhaust nozzle through which the second gas is exhausted to the second tube from the annular anti-separation member, a first end of the exhaust nozzle formed within the annular anti-separation member and fluidly coupled to the exhaust conduit, a second end of the exhaust nozzle extending from the annual anti-separation member and adapted to couple to the second tube.

\* \* \* \* \*